United States Patent [19]

Bengtsson

[11] 3,954,115

[45] May 4, 1976

[54] COMBINED TOOTH PICK AND TOOTH CLEANING IMPLEMENT

[76] Inventor: Sigurd Walter Bengtsson, Bruksgatan 17, 414 51 Goteborg, Sweden

[22] Filed: Sept. 22, 1975

[21] Appl. No.: 615,572

[30] Foreign Application Priority Data

Sept. 24, 1974 Sweden.............................. 119611

[52] U.S. Cl. ............................................... 132/89
[51] Int. Cl.². ........................................ A61C 15/00
[58] Field of Search...................... 132/89, 93, 76.4; 32/46

[56] References Cited
UNITED STATES PATENTS

| 469,064 | 2/1892 | McKay | 132/90 |
| 2,477,194 | 7/1949 | Millard | 132/93 |
| 2,931,370 | 4/1960 | Jackson | 132/89 |

*Primary Examiner*—G. E. McNeill
*Attorney, Agent, or Firm*—Hill, Gross, Simpson, Van Santen, Steadman, Chiara & Simpson

[57] ABSTRACT

For dental hygiene an implement is provided, which can pick interproximal spaces, as well as scrape the tartar off teeth faces. The implement is made of resilient material, is small, handy and inconspicuous. An instrument according to the invention comprises a cleaning portion having a channel shaped cross section tapering into a point, as well as a picking portion formed unitary therewith, so each portion can serve as a handle for the other portion. The side faces of both portions are partly roughened in order to provide an abrading surface.

2 Claims, 3 Drawing Figures

3,954,115

COMBINED TOOTH PICK AND TOOTH CLEANING IMPLEMENT

BACKGROUND OF THE INVENTION

1. This invention relates to a combined toothpick and tooth cleaning implement.

2. Prior Art

In order to remove foreign substance from interproximal dental spaces a tooth pick, i.e. a pointed, solid tool has been used. A tooth pick is, however, insufficient to remove tartar and other coatings on the teeth, and therefore so called teeth cleaners, suitable for scraping or abrading the teeth faces, have been provided. These cleaners, which must be resilient in order to fit into interproximal spaces of different widths, are designed with a mainly triangular cross section, and are often channel shaped so the cleaner, by elastic deformation of its side walls, shall have a possibility to adapt its cross section to spaces of various form.

The interproximal space between certain teeth is often so narrow that it is difficult to introduce a cleaner therein.

SUMMARY OF THE INVENTION

An implement enabling picking as well as cleaning activity is provided. In order to obtain satisfactory resiliency, without any risk of formation of splinters which would damage the gum tissue, a fine quality of synthetic resin is used. For reasons of saving space and reducing the consumption of such expensive material as small an implement as possible is provided. The implement must provide a good grip for use in two different positions of use.

A combined tooth pick and tooth cleaning implement manufactured of synthetic resin according to the invention comprises a cleaning portion having a channel shaped cross section, tapering into a thin tip, and having outwardly roughened side faces, as well as a picking portion, having a solid cross section and likewise tapering into a tip, said cleaning portion, along its open side, being substantially plane, and said picking portion being formed as a planar, leaf-like elongation of said open side, having a tapering contour with a base about equal to the biggest breadth of the cleaning portion.

The picking portion preferably occupies somewhat less than one half of the full length of the implement.

DESCRIPTION OF THE PREFERRED EMBODIMENT

Figure 1:
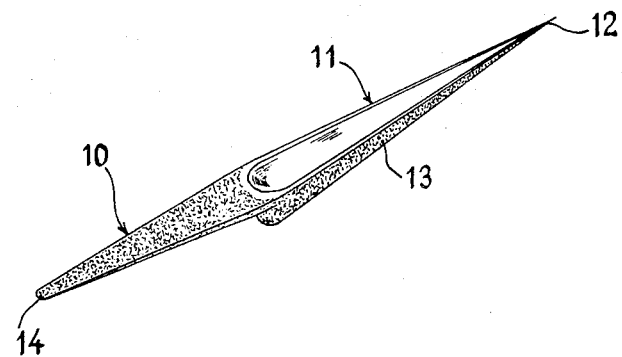
FIG. 1 is a perspective view of a combined toothpick and cleaner.
Figure 2:
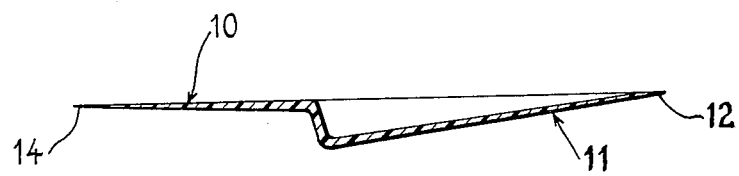
FIG. 2 is a longitudinal section through the same.
Figure 3:
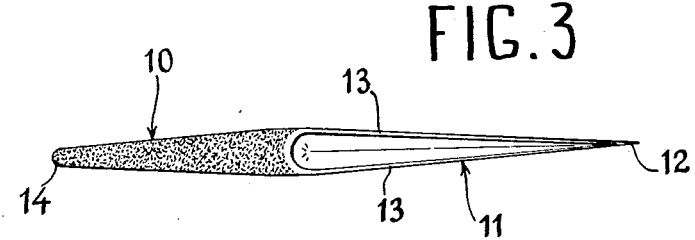
FIG. 3 shows the implement as viewed from the open side of the cleaner channel.

The implement shown in the drawing is manufactured from a synthetic resin material having such properties as to make the implement pliable and resiliently deformable. It comprises a picking portion, generally denoted by 10, and a cleaning portion, generally denoted by 11. The latter is channel shaped, having a substantially triangular cross section, having its biggest dimensions at its end which merges into the picking portion, and tapering outwardly in the direction of its tip 12, which may be shaped as a fine point or be slightly chisel shaped.

The channel is defined by two side walls 13, the outwardly faces of which are roughened or knurled, whereby a scraping or abrading action will be brought about when the cleaning portion is reciprocated in an interproximal space. Due to the elastic properties of the material the side walls 13 will individually adapt themselves to the juxtaposed teeth faces. The face of the cleaning portion defining the open side of the channel is straight and should be turned toward the gum, while the ridge of the channels slopes down into the tip.

The picking portion is formed as a flat leaf being an extension of the straight side of the cleaning portion. The leaf has a base equal to the broadest dimension of the cleaning portions, and tapers, as well as becomes thinner in the direction of its chisel shaped tip 14. The picking portion preferably is somewhat shorter than one half of the total length of the implement, and its side faces are likewise roughened, at least over a substantional part of its extension between the base and the tip. The picking portion will thus be able to perform a limited cleaning function in narrow interproximal spaces.

The ends of the implement will have to be used in planes which are perpendicular to each other, and it is essential that a good grip for the hand is obtained for both manners of use. The roughened side faces of the cleaner and the substantial thickness of the same as it merges into the picking portion provides a good grip immediately at the base of the picking portion, so it will be possible to obtain a good guidance for bringing the picking portion into the desired location. By forming the picking portion as an elongation of the straight side of the cleaning portion to be turned toward the gum, a good grip is obtained during cleaning operations due to the broad shape of the picking leaf as well as due to the end face of the cleaning channel, which is perpendicular to the side faces of the leaf, and provides a support for the thumb or the index finger, respectively, depending upon the implement's being used in the upper or in the lower jaw.

By the shape selected an implement is provided which covers the common needs, which requires a small space in a package, and where the consumption of material is low.

What I claim is:

1. A combined tooth pick and tooth cleaning implement made of resilient synthetic resin material, comprising:
   a. a cleaning portion having two side walls merging into a ridge and defining a channel-shaped cross-section tapering into a first tip, the open side of the channel extending straight toward said first tip, and said ridge tapering into said first tip; and
   b. a picking portion having a solid cross-section merging at its base directly into said cleaning portion and having a tapering contour extending to a second tip, said picking portion being a planar leaf-like elongation of said open side, and said base being substantially equal in size to the greatest breadth of said cleaning portion.

2. A combined tooth pick and tooth cleaning implement according to claim 1, in which the length of said picking portion is less than one-half of the total length of the implement, its side faces being roughened at least over a substantial part of its extent from said base toward said second tip.

* * * * *